US008137388B2

(12) United States Patent
Sasing et al.

(10) Patent No.: US 8,137,388 B2
(45) Date of Patent: Mar. 20, 2012

(54) TRANSVERSE CONNECTOR FOR ROD-BASED SPINAL IMPLANTS

(75) Inventors: Jude L. Sasing, Quezon (PH); Edwin C. Madera, Caloocan (PH); Boy Midas H. Firme, Laguna (PH); Agustin G. Morales, Cebu (PH); Jose Martin S. Paiso, Las Pinas (PH); Adrian Catbagan, Quezon (PH); Ramon B. Gustilo, Minneapolis, MN (US)

(73) Assignee: Orthopaedic International, Inc., Cabuyao, Laguna (PH)

( * ) Notice: Subject to any disclaimer, the term of this patent is extended or adjusted under 35 U.S.C. 154(b) by 259 days.

(21) Appl. No.: 12/487,351

(22) Filed: Jun. 18, 2009

(65) Prior Publication Data
US 2009/0312799 A1 Dec. 17, 2009

Related U.S. Application Data

(62) Division of application No. 10/904,866, filed on Dec. 1, 2004, now Pat. No. 7,569,069.

(51) Int. Cl.
*A61B 17/88* (2006.01)
(52) U.S. Cl. .................. 606/279; 606/250; 606/278
(58) Field of Classification Search .......... 606/250–262, 606/324–326, 300–304; 439/781–784
See application file for complete search history.

(56) References Cited

U.S. PATENT DOCUMENTS

| | | | |
|---|---|---|---|
| 5,324,290 A | 6/1994 | Zdeblick et al. | |
| 5,380,325 A * | 1/1995 | Lahille et al. | 606/250 |
| 5,522,816 A | 6/1996 | Dinello et al. | |
| 5,527,314 A | 6/1996 | Brumfield et al. | |
| 5,603,714 A | 2/1997 | Kaneda et al. | |
| 5,688,275 A | 11/1997 | Koros et al. | |
| 5,716,355 A | 2/1998 | Jackson et al. | |
| 5,899,903 A * | 5/1999 | Cotrel | 606/279 |
| 6,080,156 A | 6/2000 | Asher et al. | |
| 6,096,039 A | 8/2000 | Stoltenberg et al. | |
| 6,206,882 B1 | 3/2001 | Cohen | |
| 6,231,575 B1 | 5/2001 | Krag | |
| 6,261,288 B1 | 7/2001 | Jackson | |
| 6,342,055 B1 | 1/2002 | Eisermann et al. | |
| 6,402,751 B1 | 6/2002 | Hoeck et al. | |
| 6,471,703 B1 * | 10/2002 | Ashman | 606/278 |
| 6,524,310 B1 | 2/2003 | Lombardo et al. | |
| 6,551,318 B1 | 4/2003 | Stahurski | |
| 6,755,833 B1 | 6/2004 | Paul et al. | |
| 7,122,036 B2 | 10/2006 | Vanacker | |

* cited by examiner

*Primary Examiner* — Eduardo C Robert
*Assistant Examiner* — James Palmer

(57) ABSTRACT

A spinal implant system is provided for correcting spinal abnormalities. The system involves connectors configured to fit over spinal implant rods, a transverse rod, and a locking member for fixing each connector to the spinal implant rod and transverse rod. The connector is configured such that when the locking member is in a first position, the transverse rod is temporarily fixed to the connector, and when the locking member is in a second position, both the transverse rod and spinal implant rod are fixed to the connector.

19 Claims, 12 Drawing Sheets

# TRANSVERSE CONNECTOR FOR ROD-BASED SPINAL IMPLANTS

CROSS REFERENCE TO RELATED APPLICATIONS

This is a divisional of prior application Ser. No. 10/904,866, now U.S. Pat. No. 7,569,069, filed on Dec. 1, 2004, the disclosure of which is fully incorporated by reference herein for all purposes.

TECHNICAL FIELD

The present invention is directed to spinal fixation system. In particular, the invention relates to a rod-based system in which spinal implant rods are implanted on either side of the spinal column, running roughly parallel to the spine. The invention concerns a top-loading connector assembly for linking the spinal implant rods.

BACKGROUND OF THE INVENTION

Many spinal fixation systems have been developed for use in correcting and stabilizing spinal defects and facilitating spinal fusion. Typically, one or more rods are placed adjacent the spinal column in a longitudinal direction and are fixed to the vertebrae. Such systems are described in U.S. Pat. Nos. 5,688,275 and 6,080,156.

In certain situations it is desired to provide transverse stability and rigidity to the implanted spinal rods. Such systems are described in U.S. Pat. Nos. 5,527,314, 5,716,355, and 6,551,318. Existing transverse connecting devices are generally of two types: adjustable connectors and fixed connectors. Adjustable devices have the advantage of being able to accommodate different distances between the spinal implant rods. They also allow the compression or distraction between the two spinal implant rods. However, they usually have the disadvantage of being complicated and involving several components that must be assembled during surgery. Fixed transverse connectors are generally simple and easy to use. They may be composed only of one piece with two setscrews. They may have a relatively low profile, can be loaded on top of the spinal implant rods, and can also be bent to conform to the anatomy. However, they lack the ability to adjust to different distances between the spinal implant rods. Fixed transverse connectors come in incremental lengths, which makes the inventory large. Use of both types of systems often requires attachment of the transverse connector components to the spinal implant rods prior to implanting the longitudinal spinal implant rods. This requires significant pre-operative planning and does not allow modification of the system, such as adding connectors, during the procedure.

SUMMARY

The invention pertains to a system for connecting two approximately parallel spinal implant rods together. The system includes connectors, a transverse rod for every two connectors, and an adjustable locking member for each connector. In one embodiment, the system includes at least two connectors, an adjustable locking member for each connector, and a transverse rod. Each connector has a channel, a first bore, and a second bore. The channel receives a spinal implant rod, the first bore receives the transverse rod and the second bore receives the adjustable locking member. The first and second bores are configured such that when the locking member is in a first position, the transverse rod is temporarily fixed to the connector, and when the locking member is in a second position, both the transverse rod and spinal implant rod are fixed to the connector. At least a portion of the channel and the first bore intersect allowing contact between the transverse rod and a spinal implant rod. The second bore extends into the channel.

In some embodiments, the channel is open-ended and configured such that a connector with a transverse rod in place can be top-loaded onto a spinal implant rod already positioned adjacent a spinal column of a patient. In one embodiment, the adjustable locking member is a setscrew. The setscrew may have a beveled tip and/or a beveled head. The setscrew is oriented such that counter-clockwise rotation withdraws the setscrew from the channel and moves the setscrew towards the transverse rod to fix the transverse rod to the connector, and clockwise rotation advances the setscrew into the channel, first releasing the transverse rod, then fixing both the spinal implant rod and transverse rod to the connector.

In one embodiment, the second bore is oriented at an oblique angle with respect to the first bore. In another embodiment, the second bore is oriented at an oblique angle in both the horizontal and vertical planes. In a further embodiment, the connector has a plurality of faces, and the first and second bores are in the same face.

The present invention also provides a method of stabilizing the spine. The method involves the steps of implanting spinal rods longitudinally on either side of the spinal column, placing a connector on each end of a transverse rod and withdrawing the locking member to fix the transverse rod to each connector to form a connector assembly, placing the connector assembly on the implanted spinal rods, and advancing the locking members to first release the transverse rod and then fix the spinal rod and transverse rod to the connector.

BRIEF DESCRIPTION OF THE DRAWINGS

The present invention will be further explained with reference to the appended Figures, wherein like structure is referred to by like numerals throughout the several views, and wherein.

DETAILED DESCRIPTION

The present invention combines the advantages of fixed and adjustable connectors. The components can be fixed together prior to application, allowing the system to behave like a fixed, one-piece connector, making it easy to apply. The locking members are oriented obliquely so that the device maintains a low profile. Also, like fixed connectors, it has only two locking members to tighten, simplifying the surgical procedure. Unlike other fixed connectors however, the present invention can adjust to different spinal implant rod distances. The design also allows the transverse rod to be bent to conform to the patient's anatomy. Finally, the necessary inventory is much less than that of fixed connectors, because the transverse connecting rod can be cut to the desired length during surgery.

Figure 1:
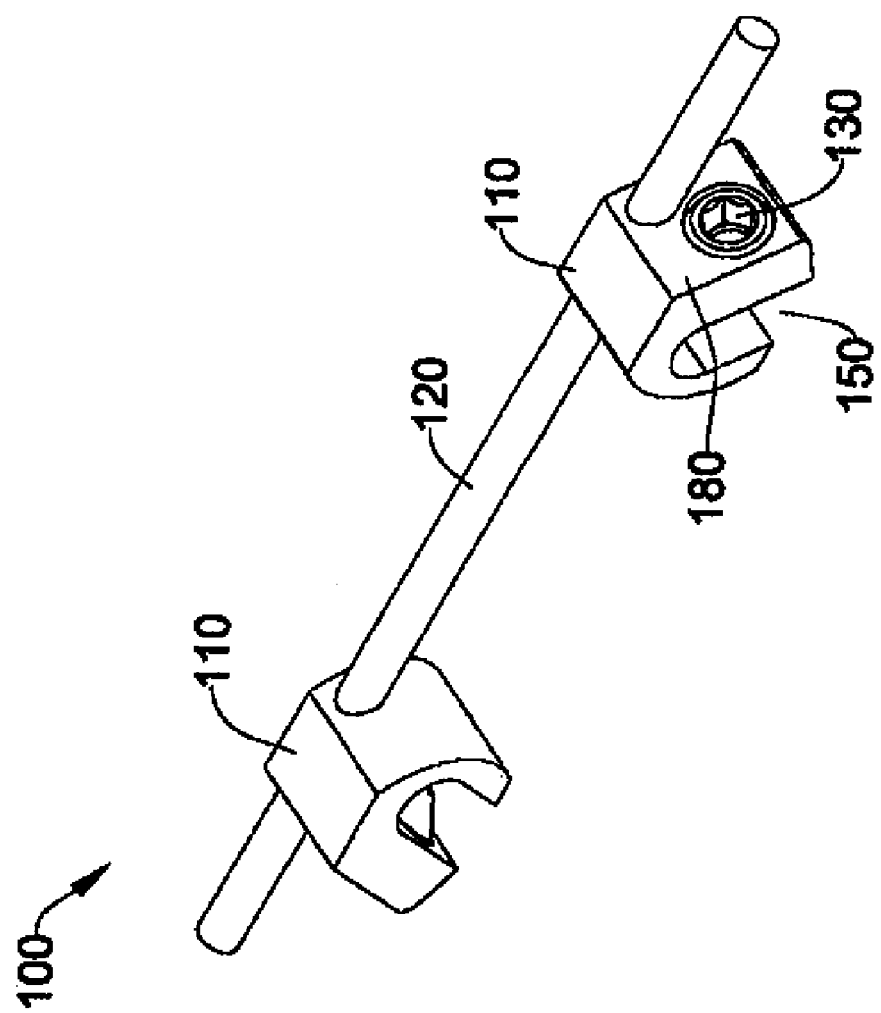
FIG. 1 is a perspective view of a spinal stabilization assembly according to one embodiment of the invention.
Figure 2:
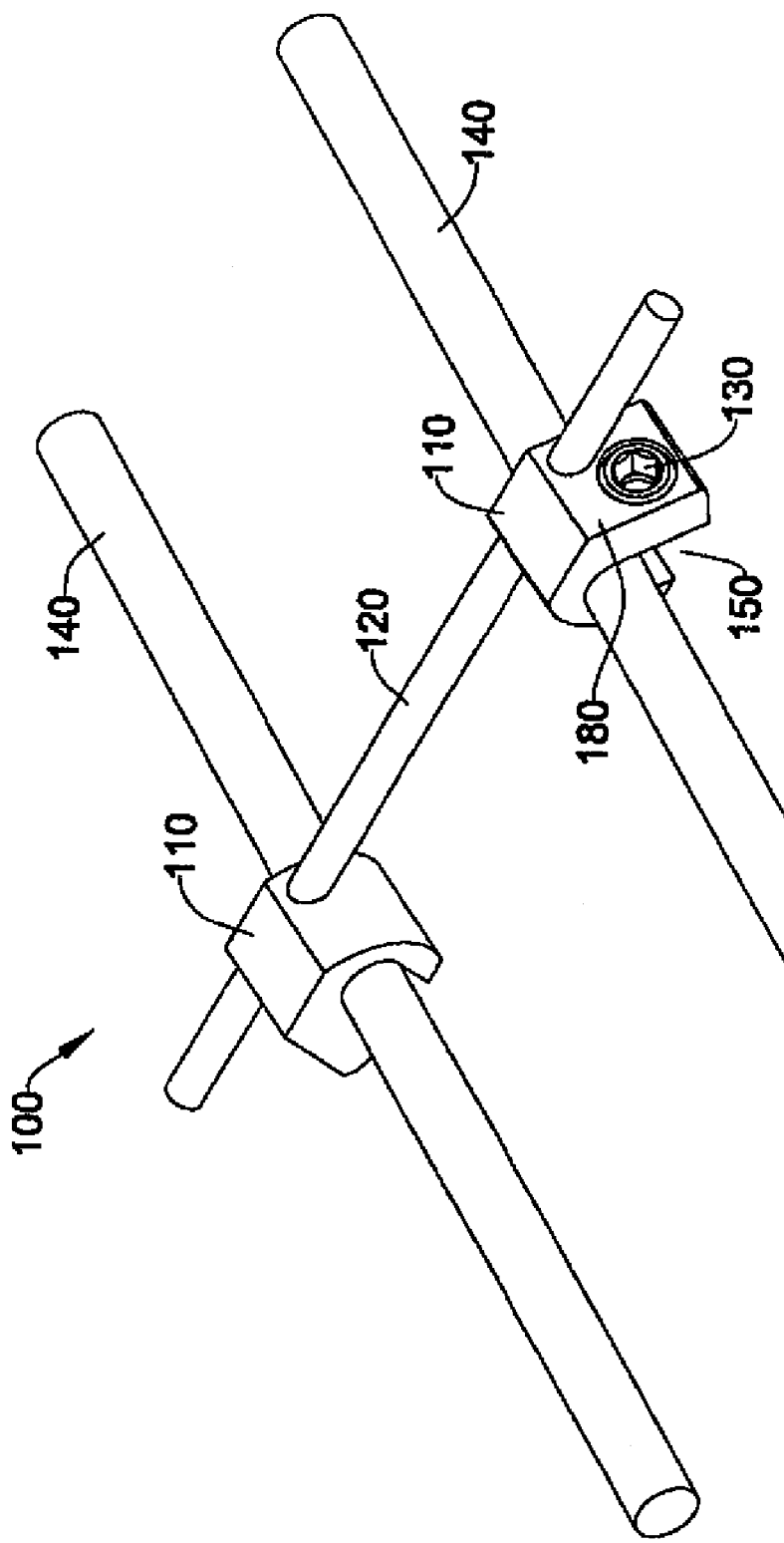
FIG. 2 is a perspective view of the spinal stabilization assembly of FIG. 1 in place on two spinal rods.
Figure 3:
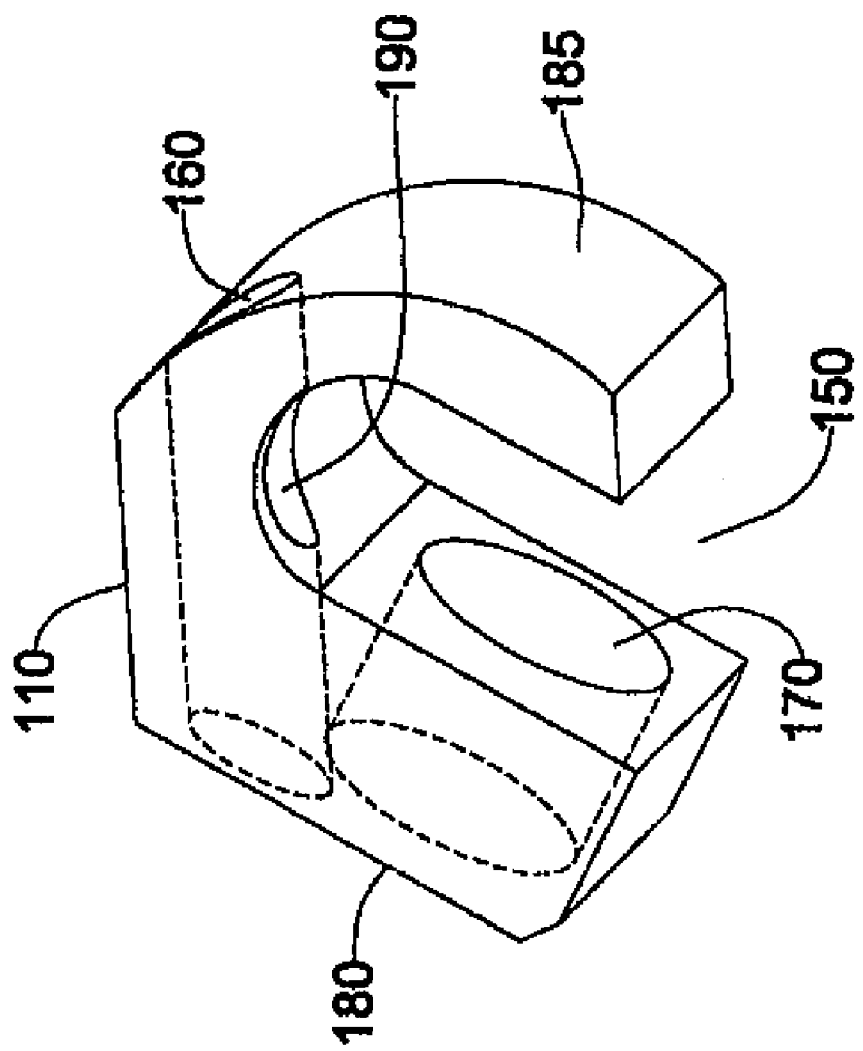
FIG. 3 is a side perspective view of a connector according to one embodiment of the invention.
Figure 4:
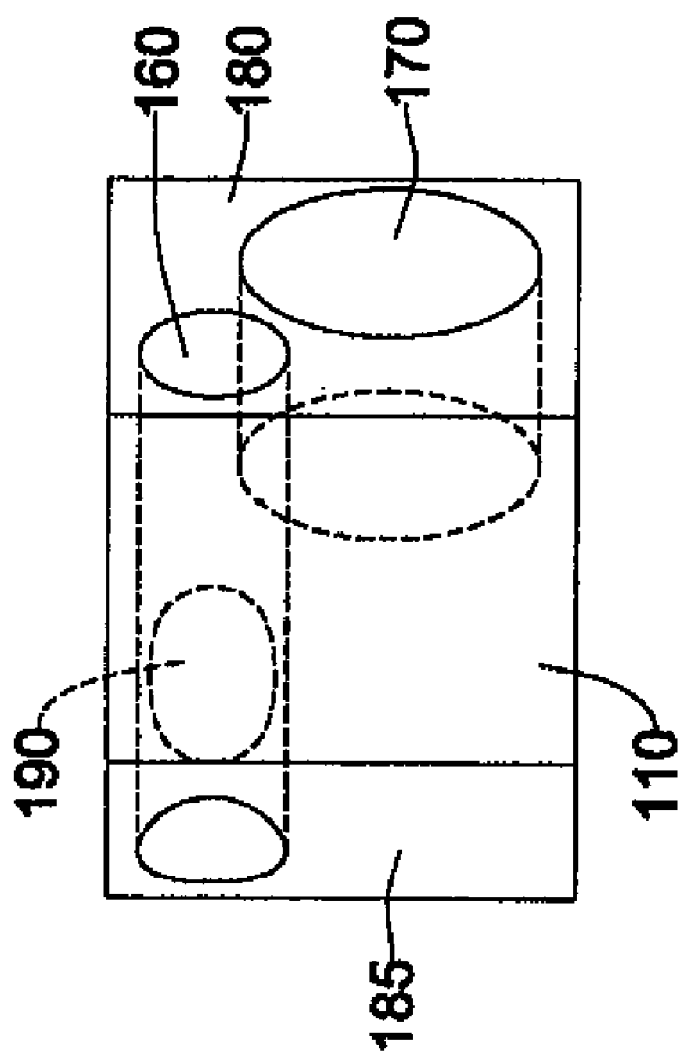
FIG. 4 is a top view of the connector of FIG. 3.

Referring now to the drawings wherein like reference numerals refer to like elements throughout the several views, FIG. 1 is a perspective view of a spinal stabilization assembly 100. FIG. 2 shows the assembly 100 in place on two spinal rods 140. The spinal stabilization assembly 100 includes two connectors 110, a transverse rod 120, and a locking member 130 for each connector. The connectors 110 each have a channel 150 that receives the spinal rod, a first bore 160 that receives a transverse rod, and a second bore 170 that receives a locking member 130. See FIG. 3.

The connector 110 can be of any shape, such as a sphere, square, rectangle, or any combination of straight and curved faces. The connector 110 has a channel 150 in one face. The channel 150 can be a groove, slot, or depression in the face of the connector 110 and is sized and shaped to received a spinal rod 140. The channel 150 is open-ended to allow the connector to be placed over a spinal rod 140 that is already fixed to the vertebrae. In some embodiments, the channel 150 is oriented at a downward oblique angle to facilitate loading the connector 110 on top of the spinal implant rod 140.

The connector 110 has a first bore 160 extending from the front surface 180 to the back surface 185 of the connector 110. The first bore 160 has an intersection region 190 where the bore intersects the channel 150. When a transverse rod 120 is inserted into the first bore 160, a portion of the rod extends into the channel 150, as shown in FIG. 7.

The connector 110 has a second bore 170 extending from the front surface 180 of the connector 110 into the channel 150. The second bore 170 is configured to receive the locking member 130. In one embodiment, the locking member 130 is a setscrew and the second bore 170 is threaded. Alternatively, the locking member 130 can be a bolt, cam-type device, or any other locking device that can be placed in a first position to fix the transverse rod 120 to the connector 110, and a second position to fix both the transverse rod 120 and spinal rod 140 to the connector 110. A bolt can function similarly to the setscrew, with advancing and withdrawing a bolt and/or nut achieving the movement between first and second positions. A cam-type locking device can have two lobes extending outward from a shaft, with the lobes offset from each other. The cam-type locking device would be turned in a first direction to fix one cam against the transverse rod, and turned in the opposite direction to release the first cam and fix the second cam against the spinal rod and transverse rod within the connector channel.

Figure 6:
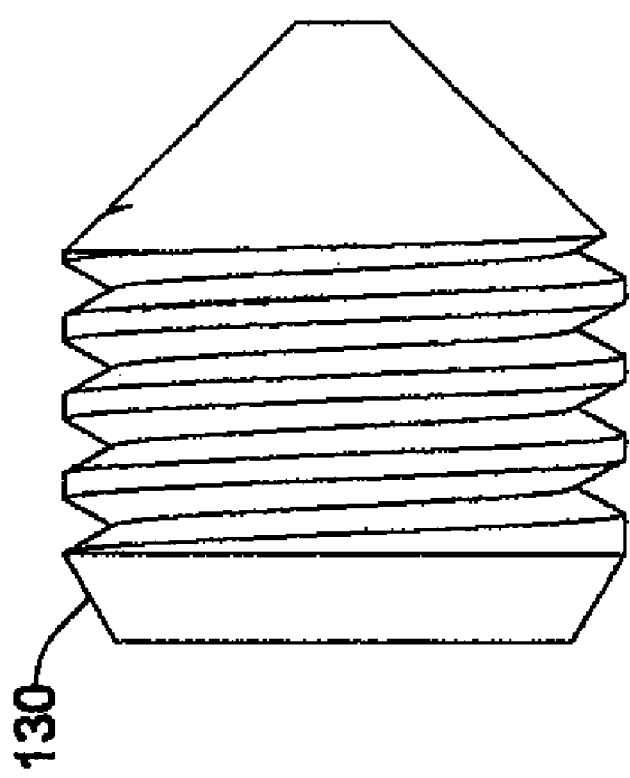
FIG. 6 is a side view of a locking member according to one embodiment of the invention.

In one embodiment, the tip of the locking member 130 is beveled, chamfered, or angled as shown in FIG. 6 so that as it moves towards the spinal implant rod 140, it impinges on it obliquely and pushes it towards the rear and top of the channel 150. The head of the locking member 130 can also be beveled, chamfered, or angled to provide a larger contact area with the transverse rod 120.

Figure 7:
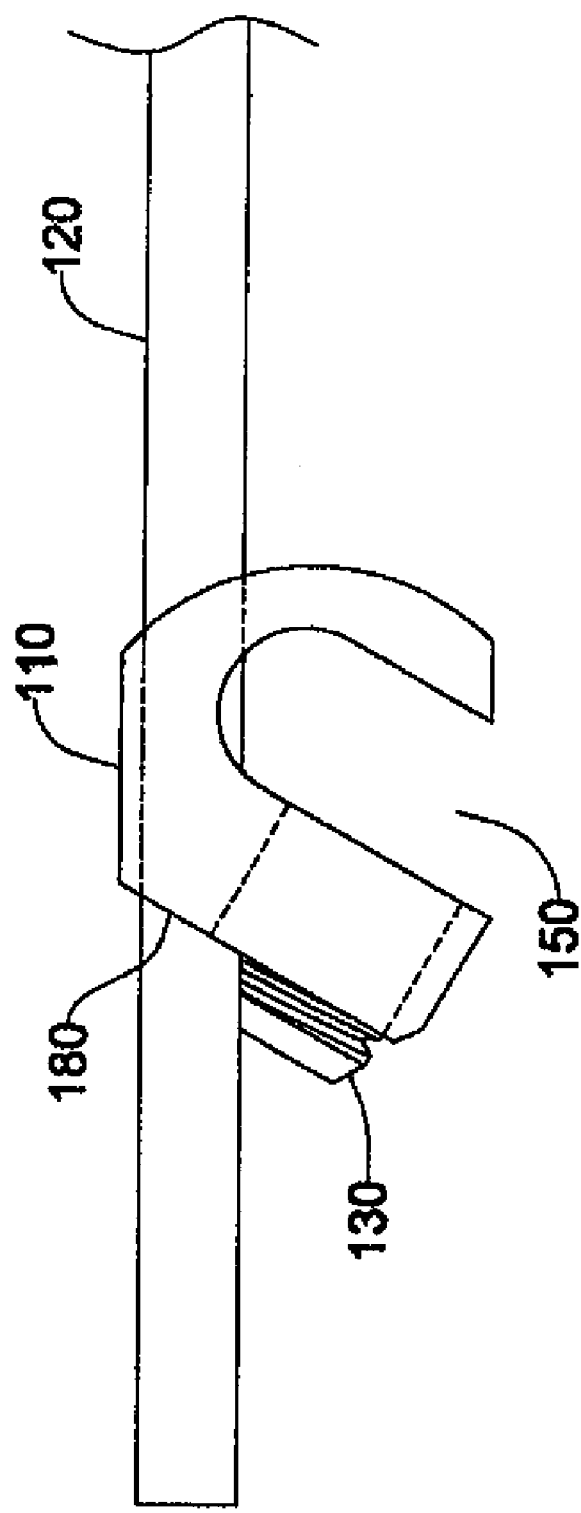
FIG. 7 is a side view of the connector of FIG. 3 with a transverse rod and locking member in the withdrawn position.

The second bore 170 is oriented at a downward angle with respect to the first bore 160, as shown in FIG. 7. The angled orientation of the second bore 170 allows a single locking member to fix a transverse rod 120 to a connector 110 prior to placing the connector 110 onto an implanted spinal rod 140, and then to fix the assembly to the spinal rod 140. The withdrawing locking member 130 contacts the transverse rod 120 at the front surface 180 of the connector. When the connector is placed on a spinal rod 140, advancing the locking member 130 temporarily releases the transverse rod 120 and causes the locking member to contact the spinal rod 140, pushing it upwards, thereby pushing the transverse rod 120 against the roof of the first bore 160. In this manner, advancing the locking member 130 towards the channel 150 fixes both the transverse rod 120 and the spinal implant rod 140 to the connector.

Figure 5:
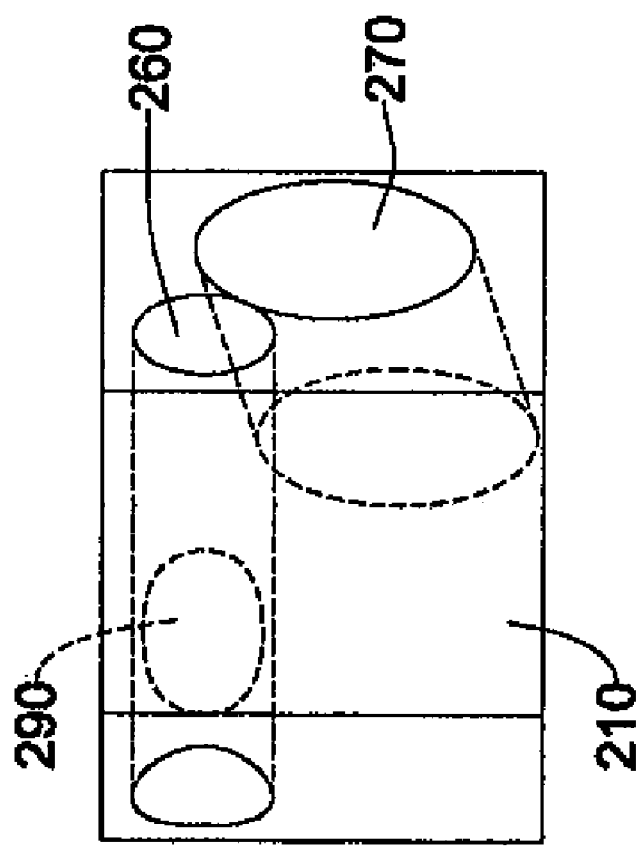
FIG. 5 is a top view of a connector according to another embodiment of the invention.

In another embodiment, shown in FIG. 5, a connector 210 has first and second bores 260, 270, and a channel 250 similar to the embodiment described above; however, the orientation of the bores is different. The second bore 270 oriented at a downward angle with respect to the first bore 260, as in the embodiment described above. The second bore 270 is oriented at a sideways angle with respect to the first bore 260, as shown in FIG. 5. The second bore 270 is thus at an oblique angle with respect to the first bore 260 in both the vertical and horizontal planes.

Figure 11:
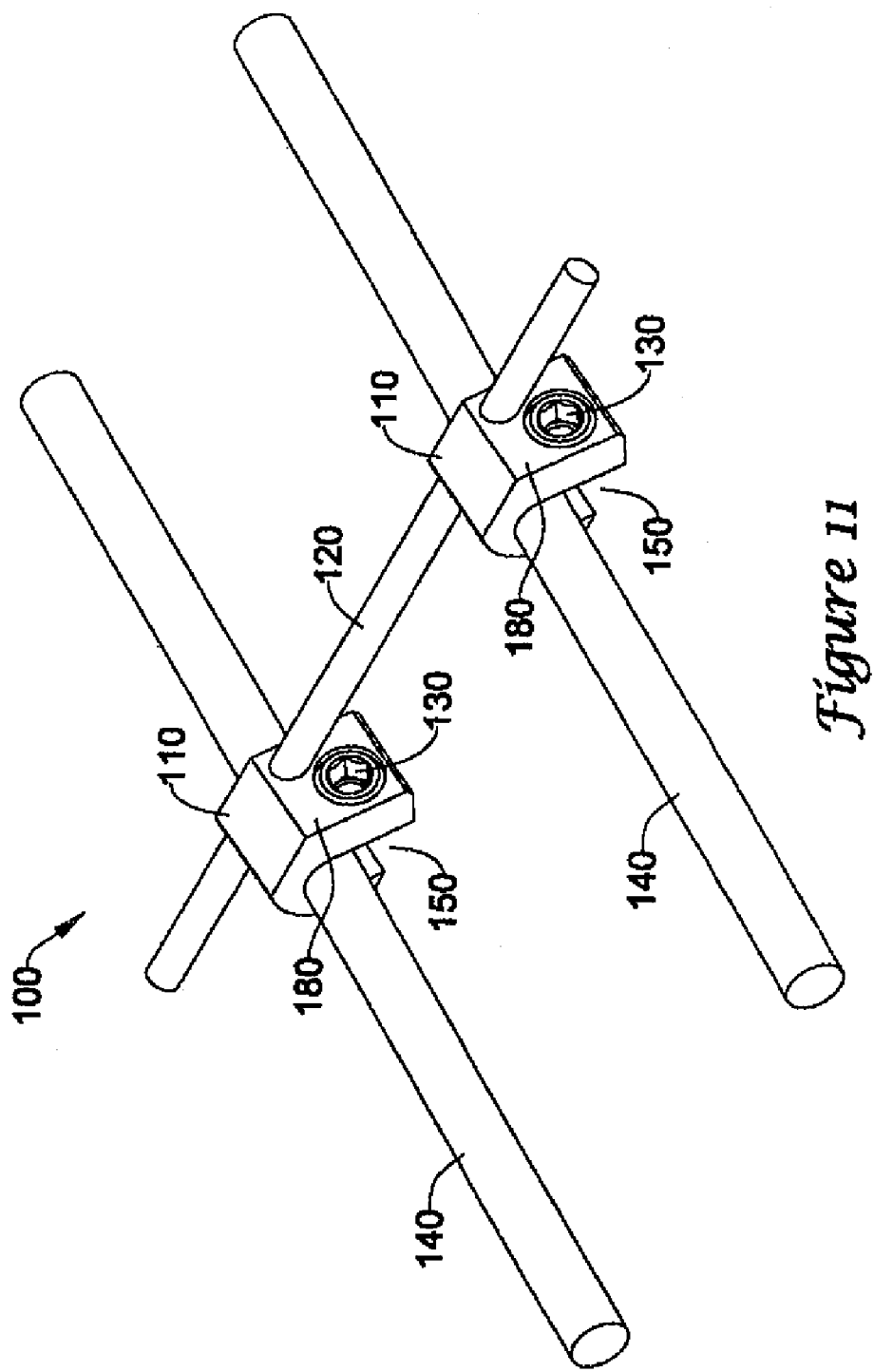
FIG. 11 is a perspective view of two connectors and a transverse rod in place on two spinal implant rods with the connectors facing the same direction.
Figure 12:
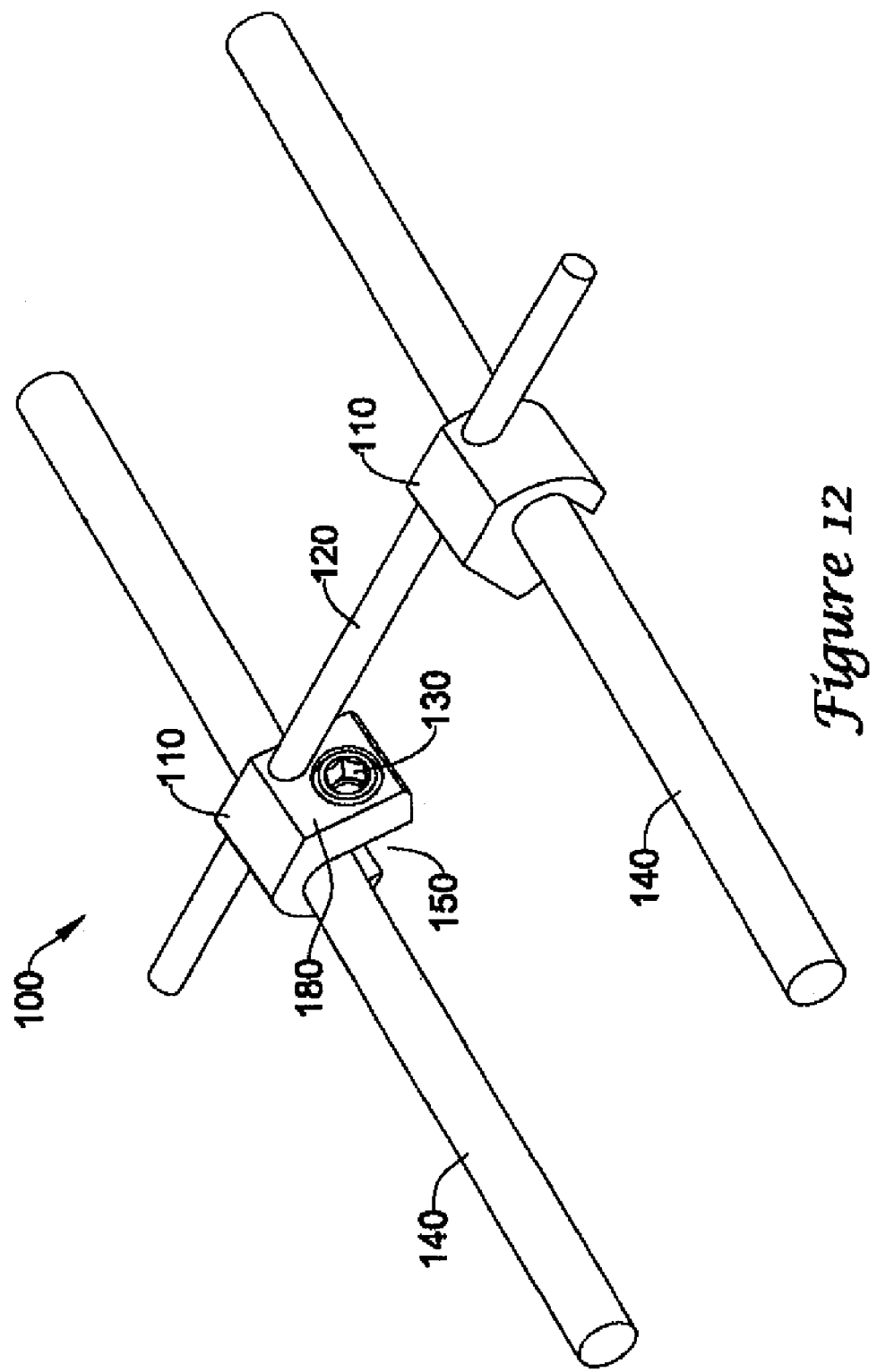
FIG. 12 is a perspective view of two connectors and a transverse rod in place on two spinal implant rods with the connectors facing each other.

In one embodiment, the two connectors 110 have the same configuration, and are placed on the spinal rods 140 facing the same direction. See FIG. 11. In another embodiment one connector is a mirror image of the other. The mirror-image connectors can be placed on the spinal rods 140 either facing outward, as shown in FIG. 1, or facing each other (inwards), as shown in FIG. 12. This provides for easy access in tightening the setscrews.

Figure 8:
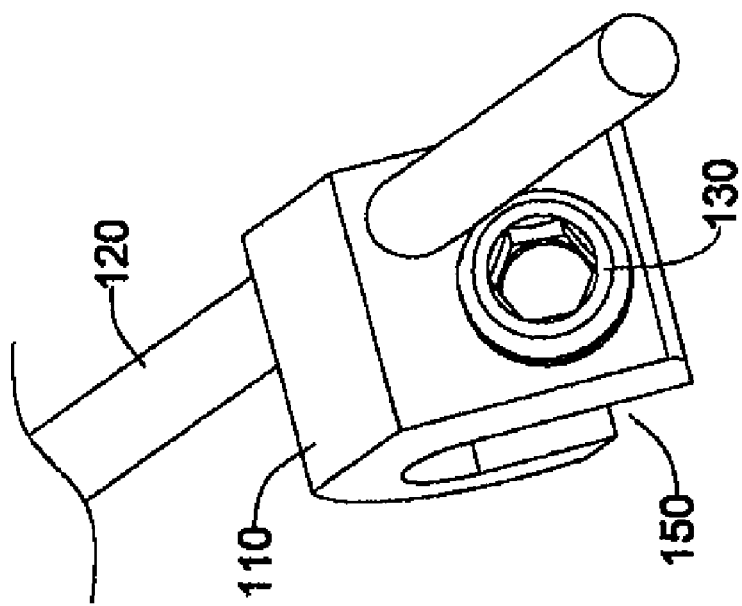
FIG. 8 is a front perspective view of the connector of FIG. 7.
Figure 9:
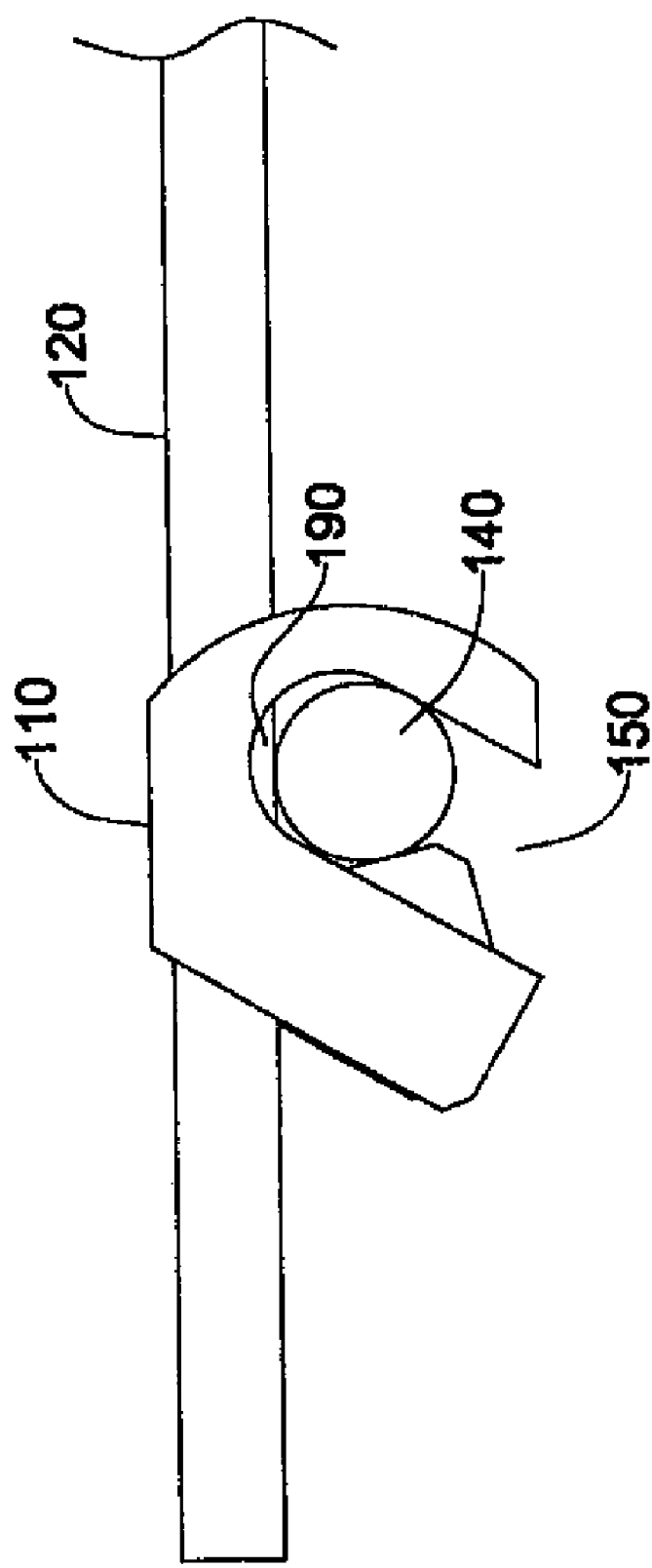
FIG. 9 is a side view of the connector of FIG. 7 with a spinal rod in place and the locking member in the advanced position.
Figure 10:
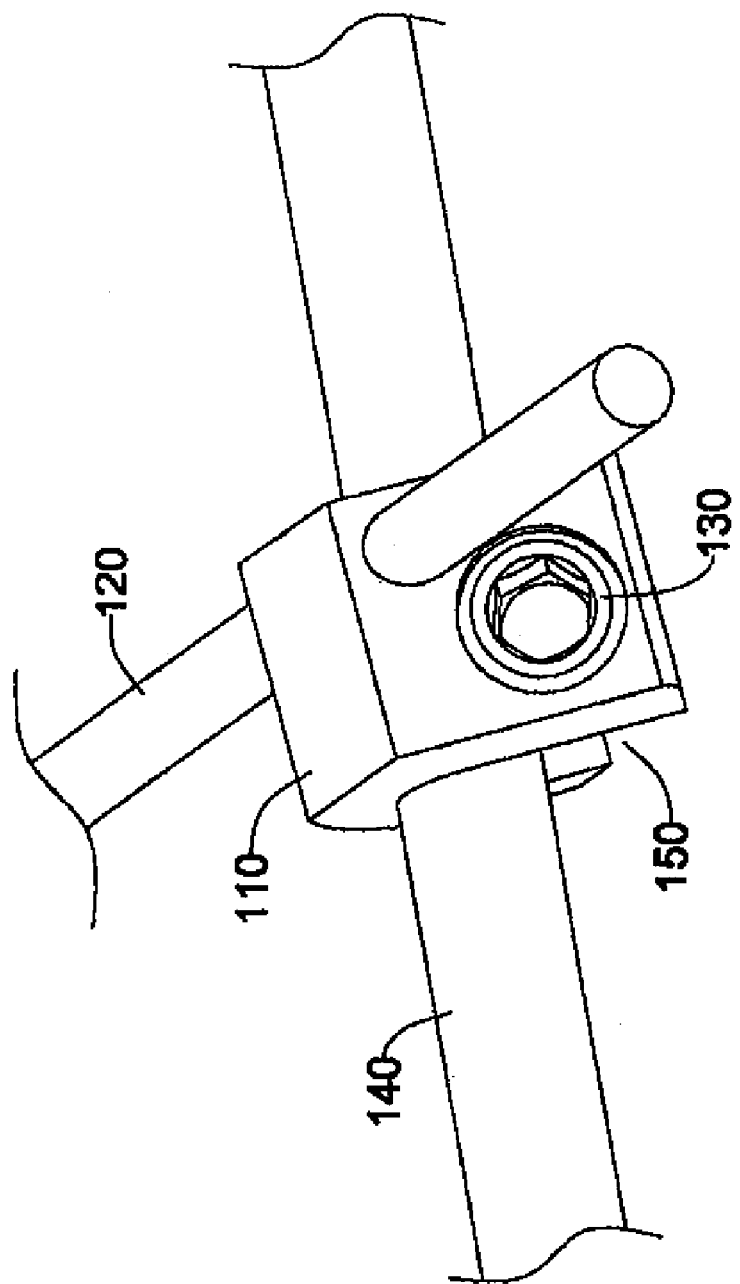
FIG. 10 is a front perspective view of the connector of FIG. 9.

In use, a locking member 130 is advanced into the second bore 170 of a connector 110, and a transverse rod 120 is placed through the first bore 160 of the connector 110, with at least a portion of the rod 120 extending outward from the front surface 180 of the connector 110. The locking member 130 is withdrawn from the second bore 170 until it contacts the transverse rod 120. In the embodiment in which the locking member 130 is a setscrew, the setscrew is generally turned counter-clockwise to withdraw it from the second bore 170, and turned clockwise to advance it. As it is withdrawn, the locking member 130 impinges on the transverse rod 120 and reversibly fixes it to the connector 110. See FIGS. 7 and 8. The connector 110 with fixed transverse rod 120 is placed over a previously implanted spinal rod 140. The locking member 130 is then advanced into the channel 150, releasing the transverse rod 120. The locking member 130 is advanced until it contacts the spinal implant rod 140 in the channel 150. The downward angle of the second bore 170 is such that the advancing locking member 130 impinges on the lower region of the spinal implant rod 140, pushing the spinal implant rod 140 upwards. The spinal implant rod 140 contacts the transverse rod 120 extending into the intersection region 190 of the channel 150 and pushes the transverse rod 120 against the top of the first bore 160. Advancing the locking member 130 thereby fixes both the spinal implant rod 140 and the transverse rod 120 to the connector 110.

A second connector 110 is then slid onto the free end of the transverse rod 120 and placed over a second implanted spinal rod 140. A second locking member 130 is advanced into the second bore 170 of the second connector 110, thereby fixing the transverse rod 120 to the second spinal rod 140. The locking members 130 can be withdrawn slightly to allow for final adjustment of the connectors on the transverse rod 120 and spinal rods 140, and then the locking members 130 are fully tightened.

In another method of use, the transverse rod 120 is fixed into two connectors 110 and then the assembly 100 is placed over two previously implanted spinal rods 140. Once the assembly 100 is in the desired position on the spinal implant rods 140, the locking member 130 in one connector 110 is advanced just enough to capture the first spinal implant rod 140. This allows the transverse rod 120 to move inside the connector 110, allowing the second connector 110 to be slid onto the second spinal implant rod 140. The locking member 130 in the second connector 110 is then advanced to capture the second spinal implant rod 140. The locking members 130 in both connectors 110 are then fully advanced to fix the transverse rod 120 to the two spinal rods 140.

The transverse connector assembly is easy to apply during surgery because the components can be fixed together prior to placement on the implanted spinal rods. The use of a single locking member that first fixes just the transverse rod to the connector, and then fixes both the transverse rod and spinal rod to the connector can simplify the surgery by reducing the number of steps to be performed.

Numerous characteristics and advantages of the invention covered by this document have been set forth in the foregoing description. It will be understood, however, that the disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A method of stabilizing the spine comprising:
   implanting first and second spinal rods longitudinally on each side of the spinal column;
   providing a stabilization device including first and second connectors and a transverse rod, each connector comprising first and second bores, a channel, and a locking member, wherein each locking member is moveable between a withdrawn and an advanced position;
   placing the first and second connectors on the transverse rod and withdrawing each locking member until the first and second connectors are fixed to the transverse rod to form a connector assembly;
   placing the connector assembly over the first and second implanted spinal rods so that the first spinal rod is positioned in the channel of the first connector and the second spinal rod is positioned in the channel of the second connector;
   advancing the locking member of the first connector until the transverse rod is released from the first connector;
   continuing to advance the locking member of the first connector until the first spinal rod and the transverse rod are fixed to the first connector;
   advancing the locking member of the second connector until the transverse rod is released from the second connector; and
   continuing to advance the locking member of the second connector until the second spinal rod and transverse rod are fixed to the second connector.

2. The method of claim 1, further comprising the step of contacting the first spinal rod with the locking member of the first connector.

3. The method of claim 2, further comprising the step of contacting the second spinal rod with the locking member of the second connector.

4. The method of claim 1, wherein the channel of the first connector comprises an open ended channel extending through the first connector, the first bore comprises a central axis and extends through the first connector from a first outside surface of the first connector to a second outside surface of the first connector, wherein at least a portion of the first bore intersects the channel of the first connector at an intersection region, the second bore comprises a central axis and extends through the first connector from the first outside surface of the first connector to an inside surface of the channel of the first connector, wherein the central axis of the first bore and the central axis of the second bore define an oblique angle wherein an imaginary extension of the first bore away from the first outside surface of the first connector and an imaginary extension of the second bore away from the first outside surface of the first connector at least partially intersect.

5. The method of claim 1, wherein the channel of the second connector comprises an open ended channel extending through the second connector, the first bore comprises a central axis and extends through the second connector from a first outside surface of the second connector to a second outside surface of the second connector, wherein at least a portion of the first bore intersects the channel of the second connector at an intersection region, the second bore comprises a central axis and extends through the second connector from the first outside surface of the second connector to an inside surface of the channel of the second connector, wherein the central axis of the first bore and the central axis of the second bore define an oblique angle wherein an imaginary extension of the first bore away from the first outside surface of the second connector and an imaginary extension of the second bore away from the first outside surface of the second connector at least partially intersect.

6. A method for stabilizing implanted longitudinal spinal rods comprising:
   providing a stabilization assembly including first and second connectors and a transverse rod, wherein each connector has a transverse rod-receiving bore, a locking member positioned in a locking member-receiving bore, and a channel, wherein each locking member is moveable between a withdrawn and an advanced position;
   placing the first connector on the transverse rod and withdrawing the locking member of the first connector to fix the transverse rod to the first connector to form a connector assembly;
   placing the connector assembly over the implanted spinal rods so a spinal rod is received in the channel of the first connector; and
   advancing the locking member of the first connector to first release the transverse rod and then continuing to advance the locking member of the first connector to fix the spinal rod and transverse rod to the first connector.

7. The method of claim 6, wherein withdrawing the locking member of the first connector results in the locking member of the first connector contacting the transverse rod outside of the first connector.

8. The method of claim 6, wherein advancing the locking member of the first connector results in the locking member of the first connector contacting the spinal rod in the channel.

9. The method of claim 8, wherein the transverse rod-receiving bore of the first connector intersects the channel of the first connector such that advancing the locking member of the first connector results in the spinal rod contacting the transverse rod, thereby fixing the spinal rod and transverse rod to the first connector.

10. The method of claim 6, further comprising the step of placing the second connector on the transverse rod of the connector assembly.

11. The method of claim 10, wherein the step of placing the connector assembly over the implanted spinal rods further comprises placing the connector assembly over the spinal rods so that a spinal rod is received in the channel of the second connector.

12. The method of claim 11, further comprising advancing the locking member of the second connector to fix the spinal rod and transverse rod to the second connector.

13. The method of claim 6, wherein the channel of the first connector comprises an open ended channel extending through the first connector, the first bore comprises a central axis and extends through the first connector from a first outside surface of the first connector to a second outside surface of the first connector, wherein at least a portion of the first bore intersects the channel of the first connector at an intersection region, the second bore comprises a central axis and extends through the first connector from the first outside surface of the first connector to an inside surface of the channel of the first connector, wherein the central axis of the first bore and the central axis of the second bore define an oblique angle wherein an imaginary extension of the first bore away from the first outside surface of the first connector and an imaginary extension of the second bore away from the first outside surface of the first connector at least partially intersect.

14. The method of claim 6, wherein the channel of the second connector comprises an open ended channel extending through the second connector, the first bore comprises a central axis and extends through the second connector from a first outside surface of the second connector to a second outside surface of the second connector, wherein at least a portion of the first bore intersects the channel of the second connector at an intersection region, the second bore comprises a central axis and extends through the second connector from the first outside surface of the second connector to an inside surface of the channel of the second connector, wherein the central axis of the first bore and the central axis of the second bore define an oblique angle wherein an imaginary extension of the first bore away from the first outside surface of the second connector and an imaginary extension of the second bore away from the first outside surface of the second connector at least partially intersect.

15. A method for implanting a stabilization assembly, the method comprising the steps of: providing first and second connectors and a transverse rod, wherein each connector has a first transverse rod-receiving bore, a locking member positioned in a second locking member-receiving bore, and a channel, wherein each locking member is moveable between a withdrawn and an advanced position; forming a spinal stabilization assembly by: placing the first connector on the transverse rod and withdrawing the locking member of the first connector to fix the transverse rod to the first connector; placing the second connector on the transverse rod and withdrawing the locking member of the second connector to fix the transverse rod to the second connector; adjusting the distance between the first and second connectors by advancing at least one of the locking member of the first connector and the locking member of the second connector; and advancing the locking member of the first connector to first release the transverse rod and then continuing to advance the locking member of the first connector to fix the spinal rod and transverse rod to the first connector, and implanting the spinal stabilization assembly.

16. The method of claim 15, wherein the step of implanting the spinal stabilization assembly comprises placing the stabilization assembly over the implanted spinal rods so a first spinal rod is received in the channel of the first connector and a second spinal rod is received in the channel of the second connector.

17. The method of claim 15, further comprising advancing the locking member of the second connector to first release the transverse rod and then continuing to advance the locking member of the second connector to fix the spinal rod and transverse rod to the second connector.

18. The method of claim 15, wherein the channel of the first connector comprises an open ended channel extending through the first connector, the first bore comprises a central axis and extends through the first connector from a first outside surface of the first connector to a second outside surface of the first connector, wherein at least a portion of the first bore intersects the channel of the first connector at an intersection region, the second bore comprises a central axis and extends through the first connector from the first outside surface of the first connector to an inside surface of the channel of the first connector, wherein the central axis of the first bore and the central axis of the second bore define an oblique angle wherein an imaginary extension of the first bore away from the first outside surface of the first connector and an imaginary extension of the second bore away from the first outside surface of the first connector at least partially intersect.

19. The method of claim 15, wherein the channel of the second connector comprises an open ended channel extending through the second connector, the first bore comprises a central axis and extends through the second connector from a first outside surface of the second connector to a second outside surface of the second connector, wherein at least a portion of the first bore intersects the channel of the second connector at an intersection region, the second bore comprises a central axis and extends through the second connector from the first outside surface of the second connector to an inside surface of the channel of the second connector, wherein the central axis of the first bore and the central axis of the second bore define an oblique angle wherein an imaginary extension of the first bore away from the first outside surface of the second connector and an imaginary extension of the second bore away from the first outside surface of the second connector at least partially intersect.

\* \* \* \* \*